United States Patent
Engel et al.

(10) Patent No.: US 8,747,753 B2
(45) Date of Patent: Jun. 10, 2014

(54) CONTROLLER FOR UV LIGHT PURIFICATION SYSTEM

(75) Inventors: Stuart Engel, Cote St-Luc (CA); Normand Brais, Rosemere (CA)

(73) Assignee: Sanuvox Technologies Inc., Saint-Laurent, Quebec (CA)

( * ) Notice: Subject to any disclaimer, the term of this patent is extended or adjusted under 35 U.S.C. 154(b) by 709 days.

(21) Appl. No.: 12/543,392

(22) Filed: Aug. 18, 2009

(65) Prior Publication Data

US 2010/0044319 A1    Feb. 25, 2010

Related U.S. Application Data

(60) Provisional application No. 61/136,204, filed on Aug. 18, 2008.

(51) Int. Cl.
*G05B 1/00*  (2006.01)
*A61L 9/20*  (2006.01)

(52) U.S. Cl.
CPC .......... *A61L 9/20* (2013.01); *A61L 2209/111* (2013.01)
USPC ........................... 422/108; 422/119; 422/121

(58) Field of Classification Search
CPC ............ A61L 2/10; A61L 2/24; A61L 9/20; A61L 2202/11; A61L 2202/14; A61L 2209/111; A61L 2209/12; A61L 2209/212
USPC ............................ 422/24, 108, 105, 119–121
See application file for complete search history.

(56) References Cited

U.S. PATENT DOCUMENTS

| | | | |
|---|---|---|---|
| 6,805,733 B2 * | 10/2004 | Engel et al. | 422/24 |
| 6,849,234 B2 | 2/2005 | Lentz et al. | |
| 2004/0100208 A1 | 5/2004 | Readio et al. | |
| 2004/0100749 A1 | 5/2004 | Lentz et al. | |
| 2008/0095661 A1 * | 4/2008 | Kohler | 422/20 |
| 2008/0156738 A1 * | 7/2008 | Albrecht et al. | 210/748 |

* cited by examiner

*Primary Examiner* — Timothy Cleveland
(74) *Attorney, Agent, or Firm* — Ladas & Parry LLP

(57) ABSTRACT

A controller for an ultraviolet (UV) purification system having UV lamps includes a sensor in communication with a given UV lamp as well as a processor in communication the sensor. The sensor provides the UV light intensity rate of the UV lamp (sensed rate) and transmits this information to the processor which compares the sensed rate with a memory stored desired UV light intensity rate (desired rate). An indicator in communication with the processor indicates when the UV lamp is producing a UV light intensity below the desired rate. Current is provided to the UV lamp by a ballast. The processor includes a memory stored predetermined UV light intensity rate (predetermined rate) that is greater than the desired rate. When the sensed rate is lesser than the predetermined rate, the current provided by the ballast is increased such that the UV lamp produces a UV light intensity at least equal to the predetermined rate.

11 Claims, 10 Drawing Sheets

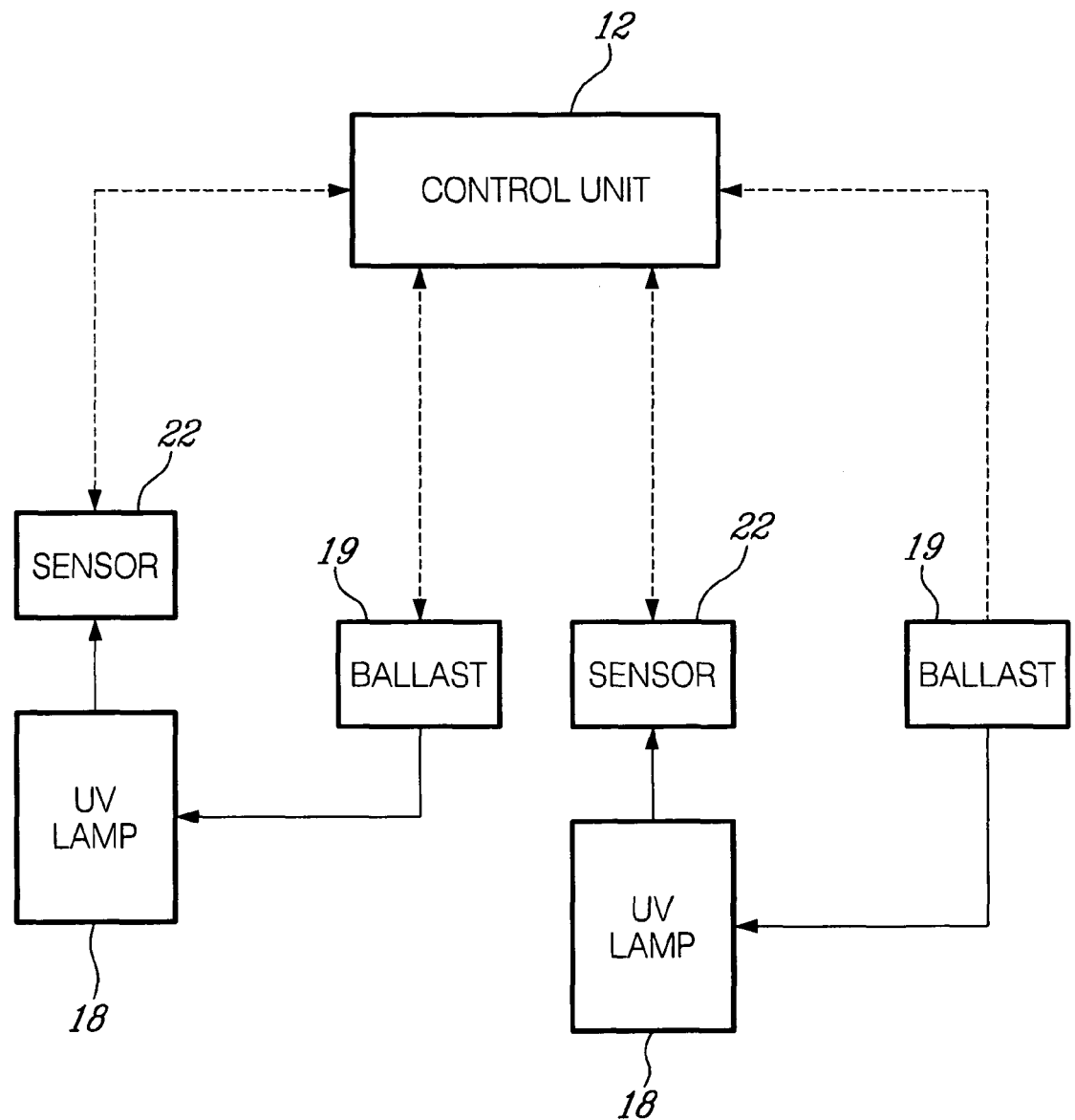

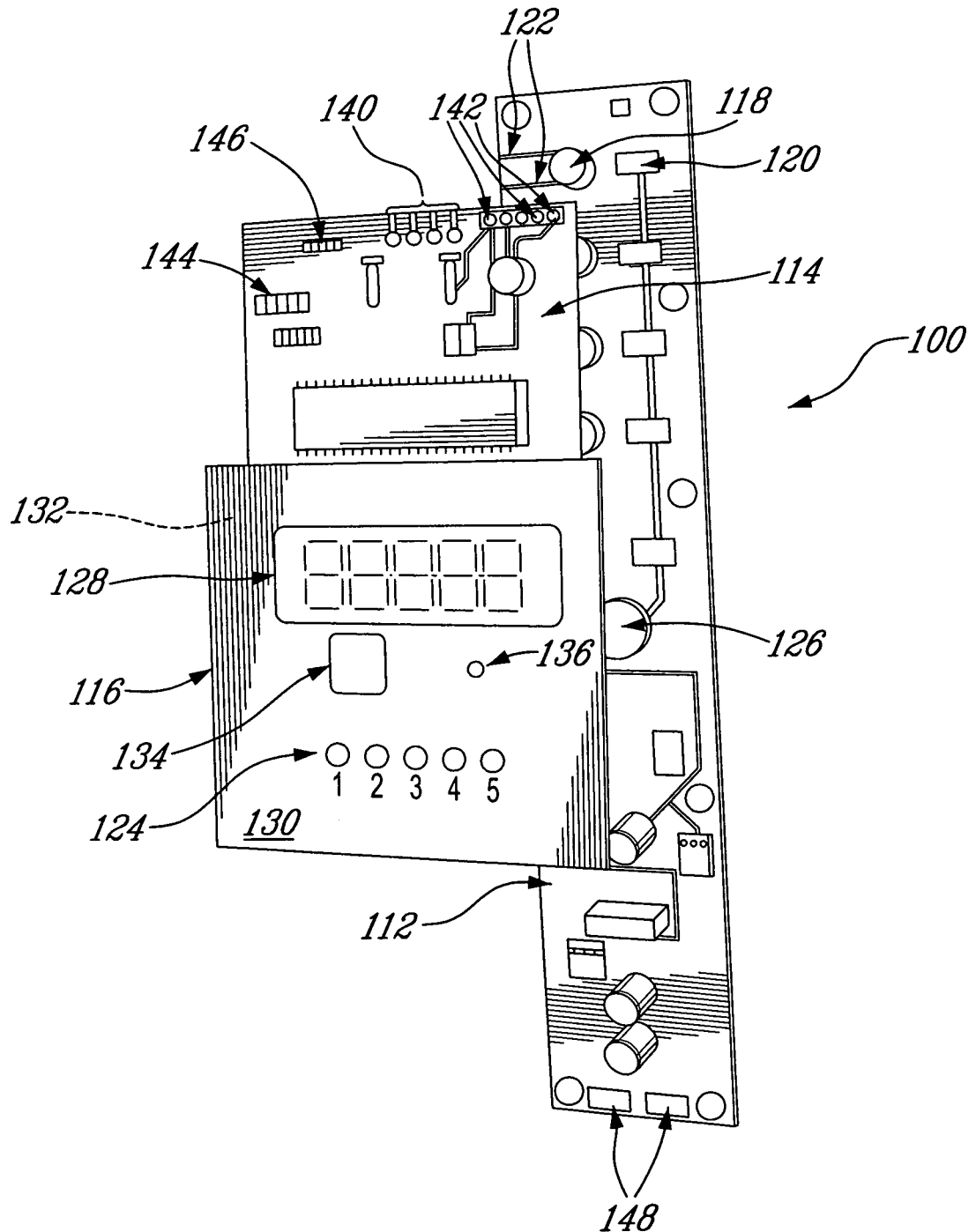

Lamp ON/Lamp OFF

Change Lamp

Purifier ON.

Bar Graph for Single & Multiple Lamp fixtures

Power ON

Day Countdown for single & Multiple Lamp fixtures

UV Intensity Meter

Lamp Out Alarm for each lamp

Lamp Reset for Single & Multiple Lamp fixtures

Carbon Dioxide Meter

VOC Detector Jet fuel, Diesel fuel, Chemical Odours, etc) with multi-stage triggers Wired/Wireless Communications

| SELECT A UNIT LOCATION | | | |
|---|---|---|---|
| Number | Location | Model | Data Installed |
| 100 | NORTH BUILDING ROON 403 | Multisplit 3D-16.5 | Aug 18, 2006 |
| 101 | WESTHOUSE BASEMENT 223 | Biowall 60 | Aug 18, 2006 |
| 102 | | | |
| 103 | | | |
| 104 | | | |
| 105 | | | |
| 106 | | Biowall 60 | JUL 19, 2006 |
| 107 | | | |
| 108 | | | |
| 109 | | | |
| 110 | | | |
| 111 | | | |
| 112 | | Biowall 60 | JUL 14, 2006 |
| 113 | | | |
| 114 | | Biowall 60 | JUL 19, 2006 |
| 115 | | Biowall 60 | JUL 17, 2006 |
| 116 | | | |
| 117 | | | |
| 118 | | | |
| 119 | | | |
| 120 | | | |
| 121 | | | |
| 122 | | | |
| 123 | | Biowall 60 | JUL 19, 2006 |
| 124 | | | |

LAMP STATUS

| Unit 101 | State | Hours |
|---|---|---|
| Lamp 1 | ON | 8 |
| Lamp 2 | ON | 8 |
| Lamp 3 | ON | 8 |
| Lamp 4 | ON | 9 |
| Lamp 5 | ON | 4415 |

Remove  Edit  Save All

RESET
TIME
BUZZER

Exit

FIG. 11

| | |
|---|---|
| Number | |
| Location | WESTHOUSE BASEMENT 223 |
| Model | Biowall 60 ▼ |
| Data Installed | Friday , August 19,2006 ▼ |

Connected
YES    NO

Lamp 1: (Lamp)    ☑    ☐
Lamp 2:    ☑    ☐
Lamp 3:    ☑    ☐
Lamp 4:    ☑    ☐
Lamp 5:    ☑    ☐

[ Save ]
[ Exit ]

FIG. 12

Are you sure you want to reset Lamp3 to 0 hours?

[ Yes ]    [ No ]    [ Cancel ]

FIG. 13

CONTROLLER FOR UV LIGHT PURIFICATION SYSTEM

CROSS-REFERENCE TO RELATED APPLICATIONS

The present application requests priority on U.S. Provisional Application No. 61/136,204 filed on Aug. 18, 2009 which is incorporated herein in its entirety.

FIELD OF THE INVENTION

The present invention is generally concerned with an ultraviolet (UV) light purification system such as an ultraviolet (UV) light air purifier and/or an UV HVAC coil purifier. More specifically but not exclusively, the present invention is concerned with a controller for monitoring the correct operation of (UV) light lamps for purification systems.

BACKGROUND OF THE INVENTION

An UV light air purifier comprises a single or a plurality of lamps producing UV light, to which ambient air is submitted so as to promote the destruction of biological and chemical contaminants found therein. Typically, the air purifier is mounted in a conduit, through which ambient air flows.

An UV HVAC Coil purifier comprises a single or a plurality of lamps producing UV light, which are mounted inside an HVAC unit and are directed onto an HVAC coil installed in the HVAC unit so as to promote the destruction, and prevent the growth of biological and chemical contaminants found therein.

There exist various systems and methods for controlling the operation of an ultraviolet air and/or an HVAC coil treatment device including an ultraviolet lamp within an air handling system. These include methods for activating the ultraviolet lamp, and determining the operational state of the air handling system.

Other devices are concerned with preventing thermal cycling of a ballast coupled to one or more lamps, such as ultraviolet and fluorescent lamps. A monitor circuit is provided to monitor activation of the ballast's thermal protection mechanism. Such monitoring may include monitoring the ballast's thermal protection mechanism, or the lamp current and ambient temperature in the vicinity of the ballast to determine that the ballast's thermal protection mechanism has been activated or not.

Still other devices are concerned with mitigating the effects of low power line voltage that can otherwise cause premature lamp mortality. A monitor circuit is provided for monitoring power characteristics relating to UV and/or fluorescent lamp operations, such as a lamp supply voltage or a current traversing the lamp. A controller operates in conjunction with the monitor circuit. The controller receives a signal indicative of the state of the monitored power characteristics. Power can be removed from the lamp during periods of brownout or other low voltage conditions to prevent accelerated lamp mortality.

A drawback of standard methods and devices for control is that they are inconvenient for quick monitoring as well as immediate control of the UV lamp(s).

OBJECTS OF THE INVENTION

It is an object of the present invention to provide a control unit for an ultraviolet (UV) purification system.

It is an object of the present invention to provide a control system for an ultraviolet (UV) purification system.

It is an object of the present invention to provide an ultraviolet (UV) purification system.

It is an object of the present invention to provide method of monitoring the operation of an ultraviolet (UV) purification system.

It is an object of the present invention to provide method of monitoring the operation of an ultraviolet (UV) purification system.

SUMMARY OF THE INVENTION

In accordance with an aspect of the present invention there is provided a control unit for an ultraviolet (UV) purification system comprising at least one UV lamp, the control unit comprising:

at least one sensor in communication with the at least one UV lamp for sensing the UV light intensity rate thereof (sensed rate);

a processor in communication with the sensor for receiving the sensed rate therefrom, the processor having in its memory a stored desired UV light intensity rate (desired rate) and providing for comparing the sensed rate with the desired rate; and an indicator being in communication with the processor for indicating when the at least one UV lamp is producing a UV light intensity below the desired rate, wherein when the sensed rate is lesser than the desired rate, the processor signals the indicator to indicate that the at least one UV lamp is producing a UV light intensity below the desired rate.

In an embodiment, the sensor is mounted to the at least one lamp. In an embodiment, the sensor is in wireless communication with the processor. In an embodiment, the sensor is in cable communication with the processor.

In an embodiment, the indicator comprises an alarm. In an embodiment, the indicator comprises a display screen. In an embodiment, the indicator comprises a signal sent to an interface.

In an embodiment, a ballast is in communication with the at least one UV lamp for providing current thereto and with the control unit for being controlled thereby, the processor having in its memory a stored predetermined UV light intensity rate (predetermined rate) that is greater than the desired rate, the processor providing for comparing the sensed rate with the predetermined rate, wherein when the sensed rate is lesser than the predetermined rate the control unit causes the ballast to increase its current output to the at least one UV lamp so as to produce a UV light intensity at least equal to the predetermined rate.

In an embodiment, the purification system comprises a plurality of UV lamps, a respective the sensor being in communication with each of the UV lamps. In an embodiment, the UV lamps of the plurality are remote from one another.

In accordance with an aspect of the present invention, there is provided a control system for an ultraviolet (UV) purification system comprising UV lamps, the control system comprising:

a plurality of the aforementioned control units, each control unit being in communication with a plurality of UV lamps via a plurality of respective sensors; and a controller being in communication with each control unit for receiving data therefrom and for control thereof, the controller comprising an interface for displaying whether or not a given one of the UV lamps is functioning below the desired rate.

In accordance with an aspect of the present invention, there is provided an ultraviolet (UV) purification system comprising:
   at least one UV lamp,
   a control unit comprising:
   at least one sensor in communication with the at least one UV lamp for sensing the UV light intensity rate thereof (sensed rate);
   a processor in communication with the sensor for receiving the sensed rate therefrom, the processor having in its memory a stored desired UV light intensity rate (desired rate) and providing for comparing the sensed rate with the desired rate; and
   an indicator being in communication with the processor for indicating when the at least one UV lamp is producing a UV light intensity below the desired rate,
   wherein when the sensed rate is lesser than the desired rate, the processor signals the indicator to indicate that the at least one UV lamp is producing a UV light intensity below the desired rate.

In an accordance with an aspect of the present invention, there is provided a control unit for an ultraviolet (UV) purification system comprising at least one UV lamp, the control unit comprising:
   a sensor in communication the UV lamp so as to read the operation thereof;
   a processor in communication with the sensor so as to receive information therefrom regarding the operation of the UV lamp;
   a display screen in communication with the processor for displaying the information related to the operation of the lamp.

In accordance with an aspect of the present invention, there is provided a method of monitoring the operation of an ultraviolet (UV) purification system comprising at least one UV lamp, the method comprising:
   sensing the UV light intensity rate (sensed rate) of the at least one UV lamp;
   providing a desired UV light intensity rate (desired rate) being the desired rate of UV light intensity that the UV lamp should be producing;
   comparing the sensed rate with the desired rate; and
   signaling when the sensed rate is lesser than the desired rate thereby indicating that the at least one UV lamp is producing a UV light intensity below the desired rate.

In accordance with an aspect of the present invention, there is provided a method of controlling the operation of an ultraviolet (UV) purification system comprising at least one UV lamp and one ballast in communication therewith for providing a current thereto, the method comprising:
   sensing the UV light intensity rate (sensed rate) of the at least one UV lamp;
   providing a desired UV light intensity rate (desired rate) being the desired rate of UV light intensity that the UV lamp should be producing;
   providing a predetermined UV light intensity rate (predetermined rate) that is greater than the desired rate;
   comparing the sensed rate with the predetermined rate;
   increasing the current output of the ballast to the UV lamp when the increase its current output to the UV lamp when the sensed rate is lesser than the predetermined rate to a current output level which causes the UV lamp to produce a UV light intensity at least at the predetermined rate.

In accordance with an embodiment, there is provided an ultraviolet (UV) air purifier and/or UV HVAC coil purifier having a controller, wherein the controller comprises a display screen linked to the UV lamp(s) of the air purifier and/or UV HVAC coil purifier so as to be able to display various information indicative of the operation and intensity of the lamp(s), to be able to determine and display information if there is a failure of the lamp(s) and/or ballast whether the failure is either the lamp(s) or the ballast, and to be able to indicate in a low voltage HVAC coil purifier if the available low voltage power is detrimental to the HVAC unit In accordance with an embodiment, there is provided a control unit for an ultraviolet (UV) air purifier and/or UV HVAC coil purifier, the control unit comprising a display screen linked to the UV lamp(s) of the air purifier and/or UV HVAC coil purifier so as to be able to display various information indicative of the operation of the lamp(s), and to be able to determine and display information if there is a failure of the lamp(s) and/or ballast whether the failure is either the lamp(s) or the ballast.

In accordance with an embodiment, there is provided a controller system for a plurality of ultraviolet (UV) air purifier and/or UV HVAC coil purifier mounted at different locations, the controller system comprising control units for each of ultraviolet (UV) air purifier and/or UV HVAC coil purifier, each control unit monitoring the operation of the lamp(s) of a given ultraviolet (UV) air purifier and/or UV HVAC coil purifier, the control units transmitting this data to the controller system, the controller system comprising a graphic user interface for displaying the data, and/or providing a signal for controlling the device.

In an embodiment, the display screen is selected from the group consisting of a digital display, an LED, an LCD screen, a touch screen or any combination thereto.

In an embodiment, there is provided a controller for monitoring the operation and status of the UV lamp(s) and ballast(s) of a UV air-purifier. and/or UV HVAC coil purifier The controller is used for monitoring and recording the status of the lamp(s); accumulating run times; displaying running hours; monitoring the status of the ballast(s), activating an alarm when a lamp failure occurs, activating an alarm when a predetermined number of operating hours has elapsed; indicating the UV intensity of a lamp, activating and deactivating the fixture(s) from a remote location; monitoring the power available for a Low Power purifier and displaying a warning and shutting down the low power purifier if there is insufficient power available, and communicating either via a wired connection, or a wireless connection (such as Zigbee Technology), with a terminal which can also be in communication with other UV light purifiers. In one version of the invention, a graphic user interface is linked to the controller so as to input instructions thereinf.

Other aspects, objects, advantages and features of the present invention will become more apparent upon reading of the following non-restrictive description of non-limiting illustrative embodiments thereof, given by way of example only with reference to the accompanying drawings.

BRIEF DESCRIPTION OF THE DRAWINGS

FIG. 8 is a schematic representation of control unit linked to sensors and ballast which are in turn linked to respective UV lamps of an ultraviolet purifier system in accordance with a non-restrictive illustrative embodiment of the present invention;

FIG. 9 is a schematic representation of control unit and circuit board thereof for ultraviolet purifier system in accordance with another non-restrictive illustrative embodiment of the present invention;

FIG. 10 is a schematic representation of an LCD screen used by the control unit of FIG. 9 in accordance with a non-restrictive illustrative embodiment of the present invention; and FIGS. 11 to 13, show interface displays in accordance with the graphic user interface used by the control unit of FIG. 9 in accordance with a non-restrictive illustrative embodiment of the present invention.

DESCRIPTION OF ILLUSTRATIVE EMBODIMENTS

A UV light air purifier comprises a single lamp or a plurality of lamps producing UV light, to which ambient air is submitted so as to promote the destruction of biological and chemical contaminants found therein. Typically, the air purifier is mounted in a conduit, through which ambient air flows. Conduits may include a self contained unit, such as a portable or wall mounted unit, an internal building wall structure. Of course, the UV air purifier can be a stand alone unit as well. An UV HVAC Coil purifier comprises a single lamp or a plurality of lamps producing UV light, which are mounted inside an HVAC unit and are directed onto an HVAC coil installed in the HVAC unit so as to promote the destruction, and prevent the growth of biological and chemical contaminants found therein.

Generally stated, non-exclusive embodiments of the present invention are concerned with a controller for an ultraviolet (UV) light air purifier and/or UV HVAC coil purifier. The controller monitors the correct operation of one or more lamps which are enclosed in the conduit or in the HVAC unit and not readily accessible to standard inspection. The controller of the present invention is used for, without limitation: monitoring the UV intensity level of each lamp so that is performs above a given threshold level and providing a signal when a given lamp is under this threshold level; monitoring and recording the status of the lamp and/or the ballasts that power the lamps; accumulating run times; displaying running hours; activating an alarm when a lamp and/or ballast failure occurs; activating an alarm when the lamps have reached a predetermined period of accumulated time; monitoring and recording the intensity of the ultraviolet lamps; and communicating with a terminal which can also be in communication with other UV light purifiers and/or UV HVAC coil purifiers. In one version of the invention, a graphic user interface (i.e. an LCD screen, touch screen etc.) is linked to the controller so as to input instructions therein. Still more specifically, the present invention is used on UV air-purifiers and/or HVAC coil purifiers to monitor the status of the lamp(s) and ballast(s).

With reference to the appended drawings, illustrative embodiments of the present invention will be described herein so as to exemplify the invention and by no means limit the scope thereof.

Figure 1:
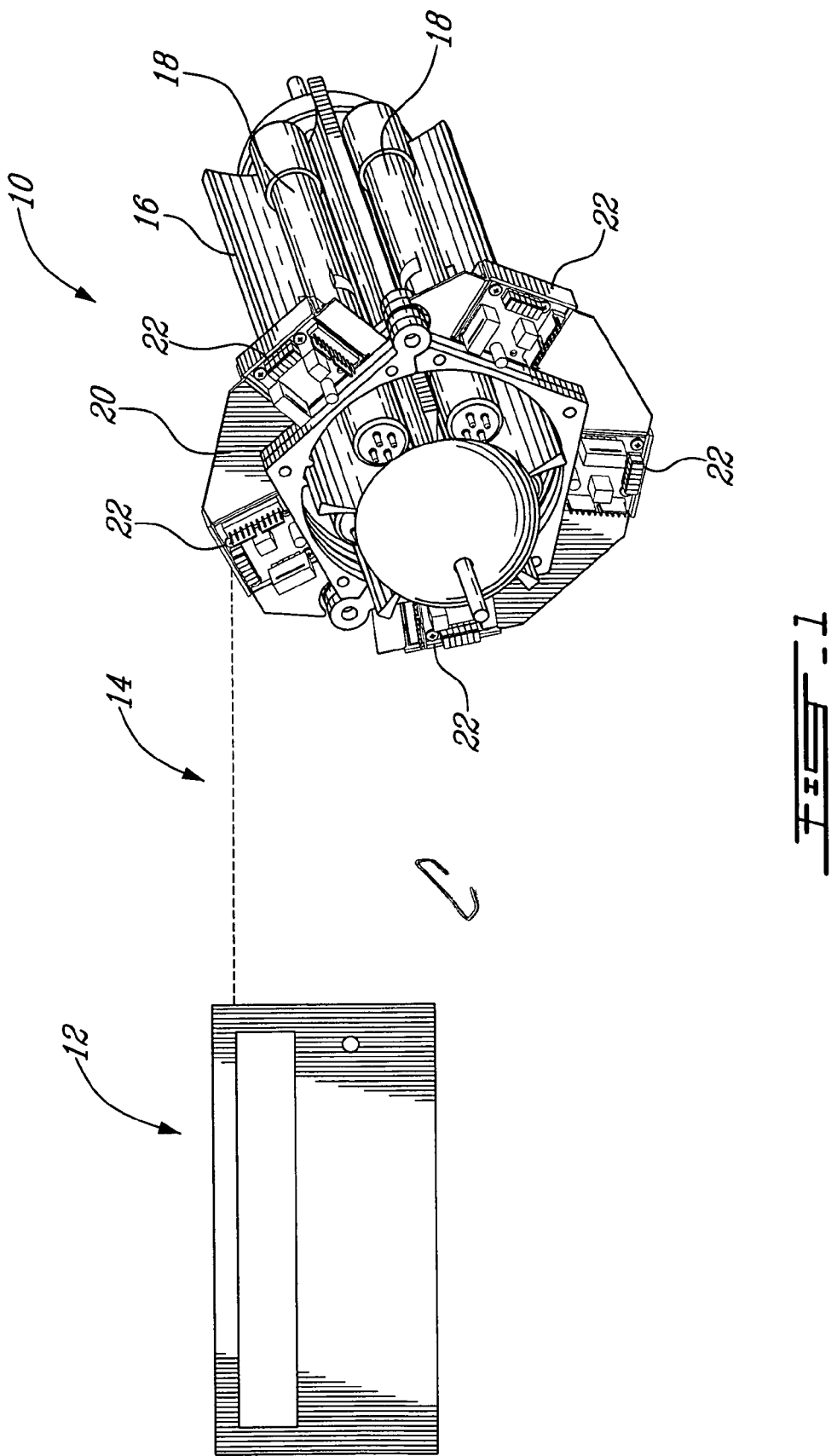
FIG. 1 is a schematic representation of a control unit linked to a UV lamp assembly of an ultraviolet purifier system in accordance with a non-restrictive illustrative embodiment of the present invention.

FIG. 1 shows a UV lamp assembly 10 linked to a control unit 12 via either a cable or wireless link 14.

The UV lamp assembly 10 includes a support 16 on which are mounted a plurality of UV lamps 18 via a clamp 20. Adjacent to each lamp 18 is a sensor 22; each sensor 22 is in communication with the control unit 12 so as to transmit data thereto and receive data therefrom.

Figure 2:
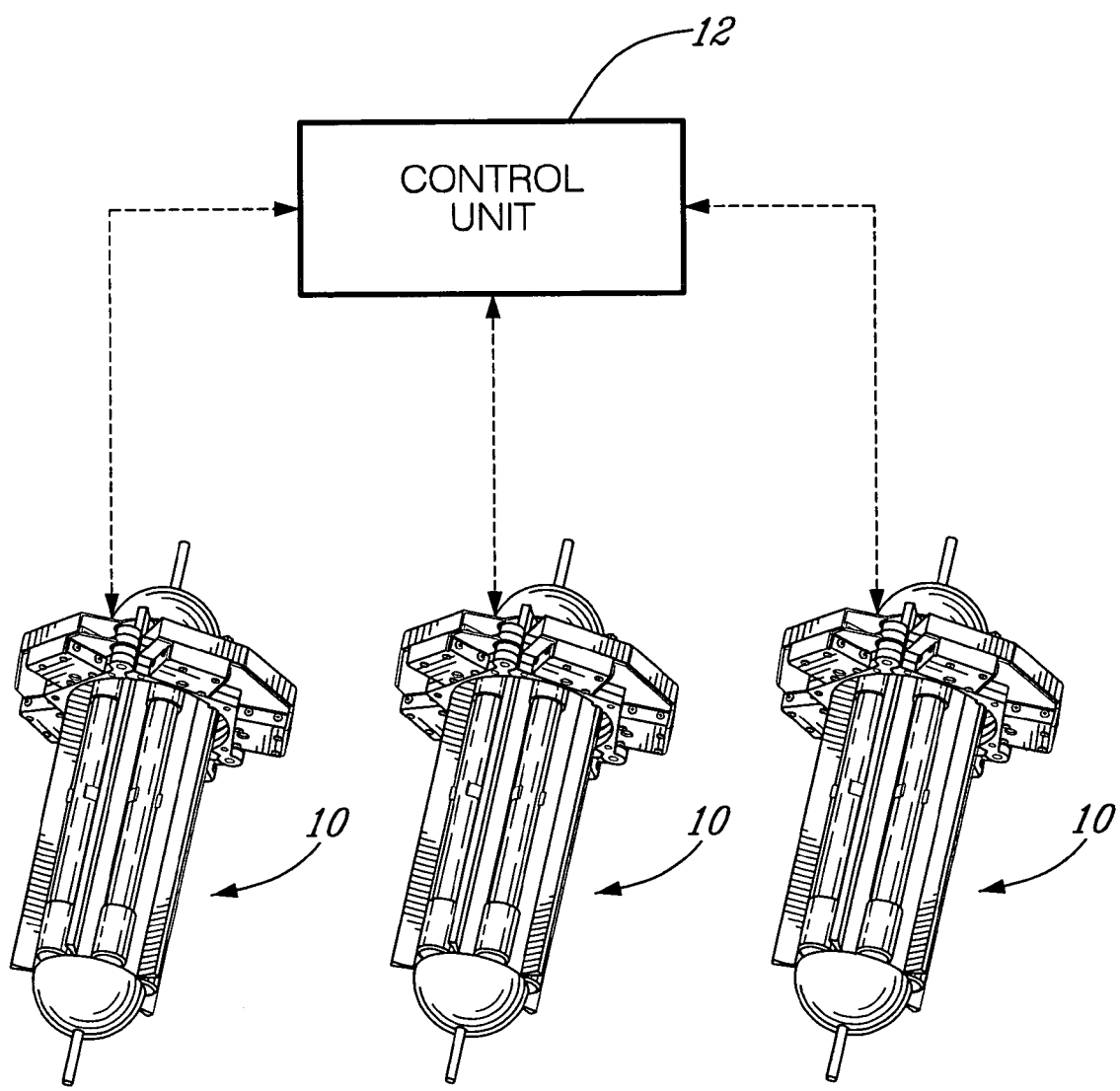
FIG. 2 is a schematic representation of a control unit linked to a plurality of UV lamp assemblies in accordance with a non-restrictive illustrative embodiment of the present invention.

FIG. 2 shows the control unit 12 being linked to a plurality of lamp assemblies 10, each lamp assembly 10 may be provided in the same building or in remote areas.

Figure 3:
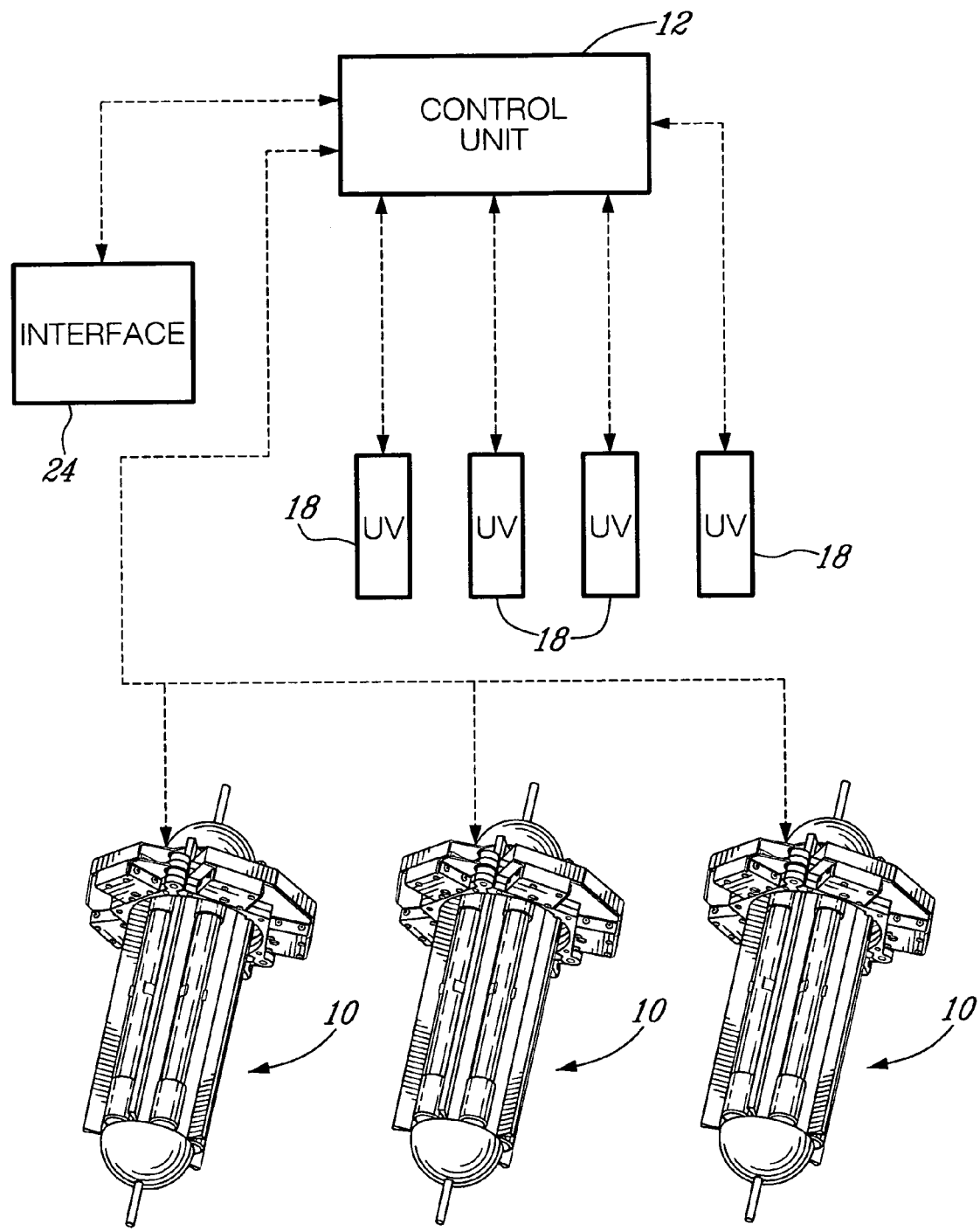
FIG. 3 is a schematic representation of a control unit linked to a plurality of UV lamps and UV lamp assemblies in accordance with a non-restrictive illustrative embodiment of the present invention.

FIG. 3 shows the control unit 12 being linked to a plurality of UV lamps 18 as well as UV lamp assemblies 10. Of course, the skilled artisan will readily understand that the assemblies 10 and lamps 18 can be in the same building or in remote locations. The control unit 12 is also linked to an interface 24 such as a computer monitor providing to monitor all data received from the various sensors 22.

Figure 4:
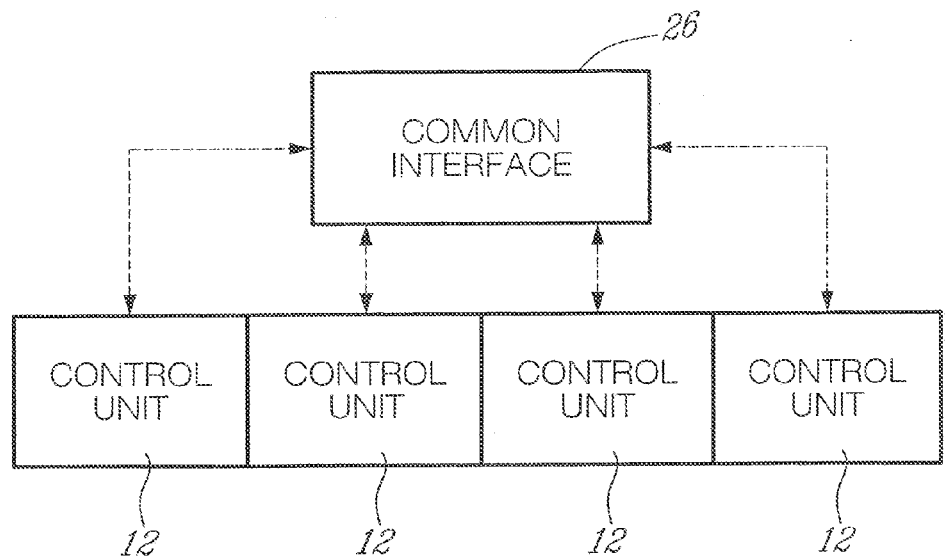
FIG. 4 is a schematic representation of a control unit linked to a plurality of control units linked to a common interface controller in accordance with a non-restrictive illustrative embodiment of the present invention.

FIG. 4 shows that a plurality of control units 10 can be in communication with a common interface 26. The control units 12 may be provided in the same location or in remote locations.

Figure 5:
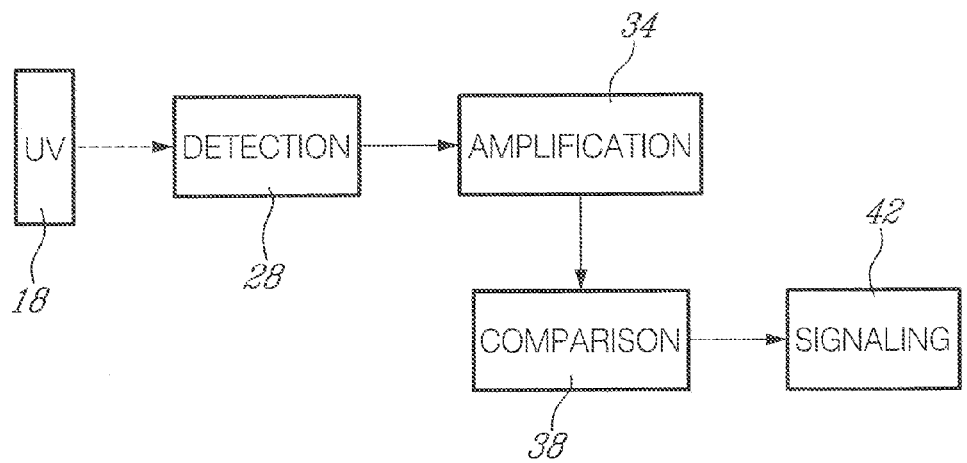
FIG. 5 is a box diagram of the method of monitoring a UV lamp of an ultraviolet purifier system in accordance with a non-restrictive illustrative embodiment of the present invention.

Having now generally described the various configurations of the links between the control boards and UV lamps 18 or lamp assemblies 20 of the present as well as the links between pluralities of control boards and a common interface, the function and structure of the control unit 12 itself will now be described in greater detail with reference to FIGS. 5 and 6.

As previously explained above, a sensor 22 is linked to a UV lamp 18 to detect the UV radiation level intensity thereof; thus the first step is the Detection (step 28) of the intensity of the UV lamp 18. The control unit 12 includes a control circuit board 30 with an input connector 32 for receiving the foregoing information from the sensor 22. The next step is the Amplification (step 34) of this information. Amplification may either be performed by the sensor 22, an amplifier (not shown) mounted to the circuit board 30 or by a processor 36. In either case, the processor 36 receives the amplified detected intensity and reads the level of UV radiation. The processor 36 then performs a Comparison Step (step 38) by comparing the actual level of UV radiation with a pre-programmed threshold that was pre-stored in the memory of the processor 36.

If a given lamp 18 has a UV radiation level below the threshold, then the processor 36 activates an indicator such as buzzer alarm 40, to provide one example, to sound off an alarm thereby signalling that a given UV lamp 18 is not working at a sufficient level (Signalling step 42). Of course, the processor 36 may send a signal to an interface 24 or 26 or to another signalling device as is known in the art.

The foregoing is more useful than signalling whether a lamp 18 is ON or OFF since even if a given lamp 18 is still functioning, it may not be functioning at a rate that is sufficient to perform its utility. For example, a given amount of radiation is needed in order to purify the air with an air purifier or to purify the various coils of HVAC and AC systems. Hence the foregoing provides for monitoring whether or not the UV lamps 18 are actually functioning at the necessary intensity or level. This skilled artisan will readily appreciate that various radiation intensities are required for different purposes as well as for different areas or surfaces that need to be purified. The above provides for maximizing the efficiency of the lamps by maintaining them maintained within a window of high purification efficacy all the while saving on energy costs since the aforementioned window avoids keeping the lamps 18 at unnecessary high levels of UV radiation.

The pre-programmed threshold level is increased or decreased (depending on the ultimate use of the UV lamps 18) via an increase switch 44 or a decrease switch 46. Of course, this is performed during the programming phase and usually when installing the control unit 12 on to the lamps or providing software to the processor 36 by way of a communication port 48. The communication port 48 can also be used to transmit data from the control unit 12 to another controller such as a computer processor connected to a monitor thereby providing the above-mentioned interface 24 or 26.

During pre-programming of the threshold the buzzer 40 is muted and as such an indicator 50 provides for indicating the number of sensors 22 that are plugged into the lamps 18

The control circuit board 30 is powered through a power inlet 52 and includes a display screen 54 which indicates which of the lamps 18 are functioning at a normal level of intensity and which lamps 18 are low (under the threshold).

As is known in the art the control circuit board 30 includes an interrupter 56, which for example may comprise dry contacts linked to the lamps 18 and relays for operating the dry contacts between open and closed states as is well known in the art. Dry contacts indicate by opening or closing a loop, whether a lamp is working or not. This indicates, remotely, the status of each lamp 18.

The control circuit board 30 also includes a power relay 57 so which can shut down the unit 12 remotely. In this way, the unit 12 can be turned off remotely. This can be combined with a safety switch which shuts down the unit 12 during maintenance.

The type of sensor 22 used can comprise a photodiode sensor, a silicon-carbide sensor or any other type of sensor known in the art for detecting the level or intensity of UV radiation.

Figure 7:
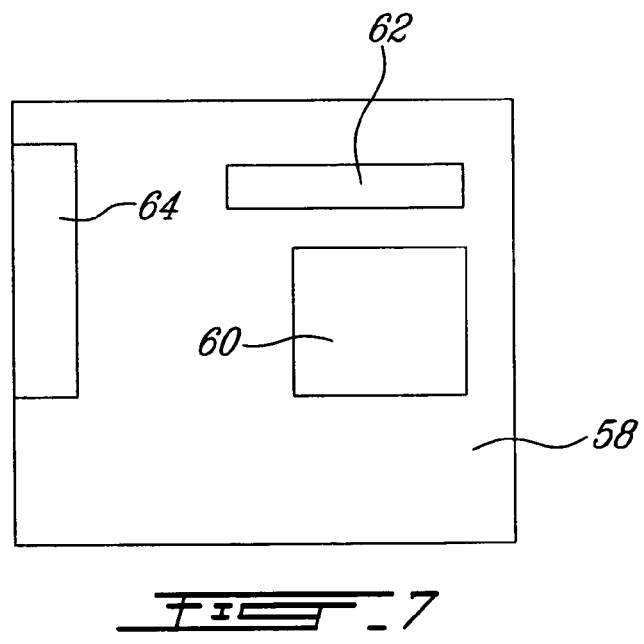
FIG. 7 is schematic representation of the circuit board of the sensor of the control unit in accordance with a non-restrictive illustrative embodiment of the present invention.

FIG. 7 shown a schematic example of a sensor 22 comprising a detector board 58 having a detector element 60 (such as a photodiode or silicon-carbide sensor). When using a plurality of sensors 22 for respective lamps 12 are used, the detector boards 58 can be connected in a daisy-chain. Jumpers 62 are provided on each board 58 so as to identify the UV intensity of each given lamp 18. A link 64 is provided between the first board 58 of the daisy-chain to the control circuit board 30.

Figure 6:
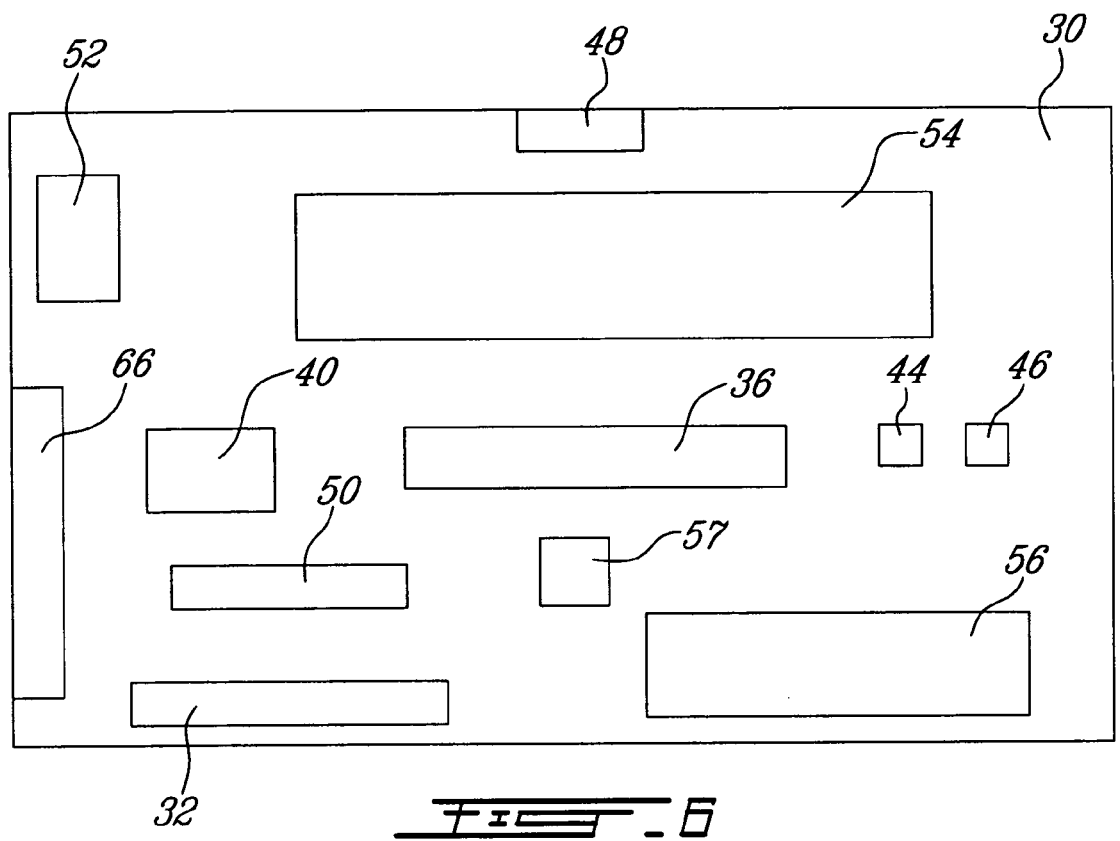
FIG. 6 is a schematic representation of the circuit board of a control unit in accordance with a non-restrictive illustrative embodiment of the present invention.

With respect to FIGS. 6 and 8, the sensor 22 can be linked to a ballast 19 that is in turn linked with the UV lamp 18 for providing current thereto. Thus, the control unit 12 can also be used in conjunction with variable power ballasts 19 in order to maintain desired UV intensity production. The foregoing links can be provided via cables or via wireless communication as is known in the art. As the UV intensity of a given lamp decreases due to but not limited to: lamp aging, lamp fouling, lamp cooling, the sensor 22 detects this decrease and sends this information to the control unit 12.

A predetermined UV intensity slightly above the aforementioned threshold is stored in the memory of the processor 36. The processor receives the UV lamp intensity rate as explained above and compares it to the predetermined UV intensity that is greater than the threshold intensity. If a match is made between the sensed UV rate and the predetermined UV rate the processor sends a signal to a ballast current controller 66 on the circuit board 30. The current controller 66 sends a signal to the particular ballast in question to increase the output current to the lamp 18 it provides current to thereby compensating for the decreased output of the lamp 18. In this way, changing a lamp 18 is avoided for a greater time period. When in fact, the lamp 18 can no longer increase its output to the necessary threshold UV intensity defined herein even though the ballast 18 is providing greater current, then the sensor 22 sends this information to the control unit 12. The processor 36 compares the sensed UV rate with its pre-stored threshold rate and then sends a signal to the buzzer 40 to sound of an alarm and/or provide another signal to computer processor with an interface 24 or 28 in order to indicate that a given lamp 18 needs to be changed The foregoing provides for: (1) maintaining a more stable lamp output; (2) increasing the replacement time of the lamp; (3) allowing the use of higher power lamps being run at lower power for a longer period of time.

With reference to the example shown in FIG. 9, a controller unit 100 is linked to an air purifier (not shown) which includes a plurality of UV lamps, in this example there are such five UV lamps, whose operation is monitored.

With reference to the example shown in FIG. 9, a controller unit 100 is linked to an HVAC coil purifier (now shown) which includes a single UV lamp, in this example there is one UV lamp, whose operation is monitored.

The control unit 100 comprises a power or control board 112 and a microprocessor board 114 which is associated with a display board 116. The power board 112 includes a switching power supply and current sensing chokes 118 which activate respective optical couplers or optocouplers 120, thereby providing an isolated signal to the microprocessor board 114. The optocouplers 120 are activated when the ballast is operating, and indicate lamp failure if deactivated, the foregoing data is provided by a current sensing inductor (or ballast current sensing terminals) 122. The current sensing inductor 122 is in series with each lamp ballast to monitor lamp current. The voltage across each inductor 122 illuminates a corresponding Light Emitting Diode (LED) 124. In the event of a lamp failure the LED 124 associated with the lamp will extinguish. The power board 112 also houses an audible lamp-failure alarm (buzzer) 126. Lamp failure also activates this audible alarm 126.

The display board 116 includes a run-time display 128 and the individual LEDs 124 (there are five LEDs 124 one for each of the five lamps), or a display board with a run time display and a single LED driven directly from the optocouplers 120 on the power board 112 which are lit as long as their associated lamps are operating. The display board 116 is fronted by a panel 130 and a descriptive membrane 132, which provides visual access to the LEDs 124, to the display 128 as well as physical access to an ALARM MUTE pushbutton 134 and a RESET pushbutton 136. The display 128 accumulates running time while power is supplied for each lamp. The accumulated time for each lamp can be reset to zero by the RESET pushbutton 36 which mechanically protected from accidental operation, such as requiring the use of a pointed device in order to discourage casual resets, as well as conveniently requiring a long reset time.

A plug-in network terminal strip 140 and connect network termination resistors 142 on the microprocessor board 114 provide for networking. Hence, a plurality of control units 100 can be linked to a controller such as a PC. Reset and monitoring can thus also be accomplished using a computer terminal via the network with the aid of a graphic user interface (GUI).

If the control units 100 are networked, the alarm 126 will sound at the host PC. It should be noted that the internal alarm 126 can be disconnected if not required or silenced via the ALARM MUTE button 34.

The control unit 100 is mounted to the back of the ballast enclosure and is configured so that the membrane/fascia of the control unit 100 is flush with the inside of the cover, and visible through a cut-out. A DIP switch 144 on the microprocessor board 114 allows for controller unit ID number to be set. The setting is arbitrary, but each location on a network should be different, and the number recorded for later reference.

The microprocessor board 114 has a number of functions which include without limitation: monitoring and recording lamp status; monitoring ballast status, accumulating run time (when power is present); displaying running hours; activating an audible alarm when a lamp and/or ballast failure occurs; selectively cancelling the audible alarm; resetting the display; and communicating via a network connection with a remote terminal in conjunction with other air purifiers.

The microprocessor board 114 also includes a programming port 146 to provide input thereto or for reprogramming thereof.

The power board 112 includes terminal lines 148 for supplying power thereto.

LCD Screens

In another embodiment of the present invention, a Liquid Crystal Display or LCD screen is used in place of the LEDs 124 and the timer display 128. As such the LCD screen which forms the display board 116 is associated to the microprocessor board 14 and to each lamp as well as each to alarms.

Therefore the schematic LCD screen 200 shown IN FIG. 10 displays the following information (without limitation thereto): Lamp ON/Lamp OFF; Change Lamp; Purifier ON; Bar Graph for Single & Multiple Lamp fixtures; Power ON; Day Countdown for single & Multiple Lamp fixtures; UV Intensity Meter; Lamp Out Alarm for each lamp; Lamp Reset for Single & Multiple Lamp fixtures; Carbon Dioxide Meter; VOC Detector (Jet fuel, Diesel fuel, Chemical Odours, etc) with multi-stage triggers; Wired/Wireless Communications, lamp failure indicator, ballast out indicator, Low Power Supply warning.

The screen 200 can also be provided in the form of a touch screen linked to all the components of the air-purifier for monitoring and touch screen control thereof.

Network Monitoring

Custom GUI software is provided on a CD with each control unit 100, to be installed at the control/monitoring terminal.

The UV monitor circuits are designed for networked monitoring. After installation of the UV air purifiers and/or UV HVAC coil purifiers, they should be configured by setting the DIP switches 144 on each control unit 100 to arbitrary, but distinct settings (unit number) so that units 100 can be distinguished and identified by the computer and operator. Units 100 can be connected to a central PC which provides a graphic user interface (GUI).

With reference to FIG. 11, on powering up the system, an opening Window A is displayed. The List-Box titled "select a unit location" gives the setup information. The system will scan, continuously (or periodically if programmed as such) the network to rest the status of each connected unit. If a unit is connected and functioning correctly, a display "WK" (Working) to the left of the unit number, indicates its status. If the unit is connected and has a failed lamp, a display "FL" (Failed) so indicates. The setup can be accomplished utilizing the buttons named "REMOVE", "EDIT", and "SAVE ALL". For any operation, select the target item in the List-Box. The "REMOVE" button will remove the item from the list. The "SAVE ALL" button will save all setup information in a file. On the next occasion when the software is started up, the saved information will be loaded automatically.

The "EDIT" button will invoke a window B shown in FIG. 12. In Window B, the setup information can be edited and will be displayed in the List-Box after clicking the "SAVE" button.

In Window A, the List-Box titled "LAMP STATUS" gives the individual lamps' status at the location highlighted in the List-Box at the top of the screen. To the right of the LAMP STATUS box, selecting the reset button "TIME" will cause the warning message in Window C to be displayed (see FIG. 13).

Clicking "YES" will clear the posted operating time for the selected lamp only (in the example shown, lamp No. 3 at location 101). This would normally only be done when a lamp is replaced. Whenever a lamp has failed, the item in the information list-Box will display "FL", and button will cancel the audible alarm will be emitted by the PC terminal. Clicking the Reset "BUZZER" button will cancel the audible alarm.

The user can exit the GUI program when Window A is displayed by clicking "EXIT" or the "X". If the setup information is changed and not saved, a message box will be displayed, prompting user confirmation.

Local Configuration

To configure the system using the LED control unit 100, the following steps should be followed:

i. If controller unit 100 is ON, it must be turned OFF ii. The ALARM MUTE button 136 should be pressed and held when the power is on until the display 128 shows a message indicative of the Configuration Mode.

iii. The ALARM MUTE button 136 should then be released.

iv. The display 128 will then scroll through a series of messages indicating each lamp;

v. A given lamp should be installed and then the user should wait until a message indicating that given lamp is displayed during scrolling, the ALARM MUTE button 136 should be pressed, held and released; the foregoing should be repeated for each lamp.

vi. Thereafter, the control unit verifies the configuration data entered. Two possibilities exist: If none of the lamps was confirmed as being installed, the control unit 100 reverts to the configuration procedure, continuing to scroll through the messages indicating the various lamps. if at least one lamp was entered as being installed, the configuration is accepted, and saved in internal memory. The unit assumes the normal operating mode.

The control unit 100 includes a UV detector such as a Photodiode (UV detector) described above that can monitor each lamp individually and that is mounted to the assembly of a purifier thereby sending feedback to a central interface so that the intensity can be read at anytime. Furthermore, a minimum UV reading can be set for each lamp of the purifier, so that an alarm can be triggered when this limit is reached, and if the alarm is disregarded, when a second or third point is reached, the unit 100 could be shut down if desired. In yet another embodiment, this Photodiode is also be used for a lamp out signal.

When using an LCD or touch screen, the control units of the present invention can be configured in other ways as is known in the art.

The various components described herein can be combined in other ways as the skilled artisan will readily understand within the context of the present invention in order to provide other non-illustrated embodiments in accordance with the present invention. More particularly the features and components of control units 12 or 100 can be combined in various ways.

It should be noted that the term "controller" should be construed to comprise, without limitation: a control unit 12, 100 or any combination of components and features thereof; a control unit 12, 100 or any combination of components and features thereof linked to an interface 24 or 26, which may include a computer processor and monitor; a plurality of controller units 12, 100 or any combination of components and features thereof, linked to an interface 24 or 26, which may include a computer processor and a monitor; a computer processor that receives information directly from sensors and/or controls the ballasts 19 directly.

It is to be understood that the invention is not limited in its application to the details of construction and parts illustrated in the accompanying drawings and described hereinabove. The invention is capable of other embodiments and of being practiced in various ways. It is also to be understood that the phraseology or terminology used herein is for the purpose of description and not limitation. Hence, although the present invention has been described hereinabove by way of embodiments thereof, it can be modified, without departing from the spirit, scope and nature of the subject invention as defined in the appended claims.

What is claimed is:

1. A kit for controlling and monitoring an ultraviolet (UV) air purification system, said kit comprising:
    a UV lamp assembly for being mounted in an air conduit and comprising:
        a support defining a plurality of longitudinal reflector/shields defining outwardly extended edges, wherein each said reflector/shield receives a UV lamp, said lamps providing constant irradiation; and
        a cuff clamp having a rigid body for being clamped onto said edges and being spaced apart from each said lamp;
    a plurality of sensors, each said sensor being mounted to said cuff clamp so as to be in aligned communication with a respective said UV lamp for continuously sensing the UV light intensity rate thereof (sensed rate);
    a processor in communication with each said sensor for continuously receiving said sensed rate therefrom, said processor having in its memory a stored desired UV light intensity rate (desired rate) and providing for continuously comparing said sensed rate with said desired rate; and
    an indicator being in communication with said processor for indicating when a said UV lamp is producing a UV light intensity below said desired rate, wherein when said sensed rate is lesser than said desired rate, said processor signals said indicator to indicate that a said UV lamp is producing a UV light intensity below said desired rate.

2. A kit according to claim 1, wherein said plurality of sensors are in wireless communication with said processor.

3. A kit according to claim 1, wherein said plurality of sensors are in cable communication with said processor.

4. A kit according to claim 1, wherein said indicator comprises an alarm.

5. A kit according to claim 1, wherein said indicator comprises a display screen.

6. A kit according to claim 1, wherein said indicator comprises a signal sent to an interface.

7. A kit according to claim 1, wherein at least one ballast is in communication with at least one said UV lamp for providing current thereto and with said processor for being controlled thereby, said processor having in its memory a stored predetermined UV light intensity rate (predetermined rate) that is greater than said desired rate, said processor providing for continuously comparing said sensed rate with said predetermined rate, wherein when said sensed rate is lesser than said predetermined rate said processor causes the ballast to increase its current output to said at least one UV lamp so as to produce a UV light intensity at least equal to said predetermined rate.

8. A control system for an ultraviolet (UV) air purification system comprising:
    a plurality of the kits of claim 1; and
    a controller being in communication with each said processor for receiving data therefrom and for control thereof, said controller comprising an interface for displaying whether or not a given one of said UV lamps is functioning below said desired rate.

9. A control system according to claim 8, wherein said kits are remote from one another.

10. An ultraviolet (UV) air purification system comprising:
    a UV lamp assembly mounted in an air conduit and comprising:
        a support defining a plurality of longitudinal reflector/shields defining outwardly extended edges, wherein each said reflector/shield receives a UV lamp, said lamps providing constant irradiation; and
        a cuff clamp having a rigid body for being clamped onto said edges and being spaced apart from each said lamp;
        a plurality of sensors, each said sensor being mounted to said cuff clamp so as to be in aligned communication with a respective said UV lamp for continuously sensing the UV light intensity rate thereof (sensed rate);
        a processor in communication with each said sensor for continuously receiving said sensed rate therefrom, said processor having in its memory a stored desired UV light intensity rate (desired rate) and providing for continuously comparing said sensed rate with said desired rate; and
        an indicator positioned outside of the air conduit and being in communication with said processor for indicating when a said UV lamp is producing a UV light intensity below said desired rate,
    wherein when said sensed rate is lesser than said desired rate, said processor signals said indicator to indicate that a said UV lamp is producing a UV light intensity below said desired rate.

11. An ultraviolet (UV) air purification system according to claim 10 further comprising a ballast in communication with at least one said UV lamp for providing current thereto and with said processor for being controlled thereby, said processor having in its memory a stored predetermined UV light intensity rate (predetermined rate) that is greater than said desired rate, said processor providing for continuously comparing said sensed rate with said predetermined rate, wherein when said sensed rate is lesser than said predetermined rate said processor causes said ballast to increase its current output to said at least one UV lamp so as to produce a UV light intensity at least equal to said predetermined rate.

* * * * *